(12) United States Patent
Mak et al.

(10) Patent No.: US 6,987,129 B2
(45) Date of Patent: Jan. 17, 2006

(54) COMPOUNDS AND METHODS FOR THE TREATMENT OF UROGENITAL DISORDERS

(75) Inventors: Vivien H. W. Mak, Palo Alto, CA (US); Stephen Grayson, San Rafael, CA (US)

(73) Assignee: Cellegy Pharmaceuticals, Inc., Brisbane, CA (US)

(*) Notice: Subject to any disclaimer, the term of this patent is extended or adjusted under 35 U.S.C. 154(b) by 0 days.

(21) Appl. No.: 10/094,409

(22) Filed: Mar. 6, 2002

(65) Prior Publication Data

US 2002/0198136 A1   Dec. 26, 2002

Related U.S. Application Data

(60) Provisional application No. 60/334,903, filed on Oct. 24, 2001, provisional application No. 60/273,901, filed on Mar. 6, 2001.

(51) Int. Cl.
*A61K 31/21* (2006.01)
*A61K 31/195* (2006.01)
*A61K 31/155* (2006.01)
*A61K 31/535* (2006.01)

(52) U.S. Cl. .................. 514/509; 514/564; 514/634; 514/228.8

(58) Field of Classification Search ............... 514/509, 514/564, 634, 228.8
See application file for complete search history.

(56) References Cited

U.S. PATENT DOCUMENTS

| | | | |
|---|---|---|---|
| 4,421,737 A | 12/1983 | Ito et al. | |
| 4,533,540 A | 8/1985 | Blank | |
| 4,559,222 A | 12/1985 | Enscore et al. | |
| 4,654,209 A | 3/1987 | Leslie et al. | |
| 4,655,766 A | 4/1987 | Theeuwes et al. | |
| 4,681,584 A | 7/1987 | Gale et al. | |

(Continued)

FOREIGN PATENT DOCUMENTS

CA     2325930 A1    7/2001

(Continued)

OTHER PUBLICATIONS

Paavonen 'Diagnosis and Treatment of Vulvodynia,' 1995, Annals of Medicine, vol. 27, No, 2, p. 175-181.*

(Continued)

*Primary Examiner*—Shengjun Wang
(74) *Attorney, Agent, or Firm*—Townsend and Townsend and Crew LLP (57) ABSTRACT

The present invention provides methods for treating a variety of urogenital disorders, such as, for example, vaginismus, dyspareunia, vulvodynia (including vulvar vestibulitis), interstitial cystitis, nonspecific urethriris (i.e., nonspecific pain and/or burning of the urinary tract) and sexual dysfunctions, such as, for example, female sexual arousal disorders and female sexual orgasmic disorders, using a variety of compounds, including, but not limited to, NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators, endothelin receptor antagonists, bisphosphonates and cGMP-dependent protein kinase activators (e.g., cGMP mimetics).

14 Claims, 1 Drawing Sheet

U.S. PATENT DOCUMENTS

| | | | |
|---|---|---|---|
| 4,784,857 | A | 11/1988 | Berry et al. |
| 5,071,656 | A | 12/1991 | Lee et al. |
| 5,565,466 | A | 10/1996 | Gioco et al. |
| 5,595,970 | A | 1/1997 | Garfield et al. |
| 5,686,099 | A | 11/1997 | Sablotsky et al. |
| 5,698,589 | A * | 12/1997 | Allen .......................... 514/509 |
| 5,731,339 | A | 3/1998 | Lowrey |
| 5,877,216 | A | 3/1999 | Place et al. |
| 5,958,926 | A | 9/1999 | Garvey et al. |
| 6,165,975 | A | 12/2000 | Adams et al. |
| 6,294,517 | B1 | 9/2001 | Garvey et al. |
| 6,306,841 | B1 | 10/2001 | Place et al. |
| 6,331,543 | B1 * | 12/2001 | Garvey et al. .............. 514/250 |
| 6,417,207 | B1 | 7/2002 | Garvey et al. |

FOREIGN PATENT DOCUMENTS

| | | |
|---|---|---|
| WO | WO 95/05172 | 12/1995 |
| WO | WO 96/27372 | 9/1996 |
| WO | WO 98/586633 | 12/1998 |
| WO | WO 99/21562 | 5/1999 |
| WO | WO 99/66909 A2 | 12/1999 |

OTHER PUBLICATIONS

Burnett, Arthur L., "Immunohistochemical Description of Nitric Oxide Synthase Isoforms in Human Clitoris," *The Journal of Urology*, vol. 158, pp. 75-78, (Jul. 1997).

Palmer, R. M. J., "Nitric oxide release accounts for the biological activity of endothelium-derived relaxing factor," *Nature*, vol. 327, pp. 524-526, (Jun. 11, 1987).

Peleg, Roni, "Glyceryl trinitrate ointment as a potential treatment for primary vaginismus," *European J. of Obstetrics & Gynecology and Reproductive Biology*, 96, pp. 111-112, (2001).

Tollins, Jonathan P., "EDRF and Regulation of Vascular Tone," *Hypertension*, vol. 17, No. 6, Part 2, pp. 909-913, (1991).

Walsh, Kathleen E., "Safety and Efficacy of Topical Nitroglycerin for Treatment of Vulvar Pain in Women with Vulvodynia: A Pilot Study," *JGSM*, vol. 5, No. 4, pp. 1-7, (Jul./Aug. 2002).

Derwent Acc No. 2001-570957 "Medicament useful for prevention and treatment of sexual dysfunction comprises potassium channel opener solutions and/or Papaverin" CA 2325930A (Chem Investment Ltd.) (Jul. 29, 2001) (Abstr.).

"Sexual Pain Disorder" at http://www.psychologytoday.com/HTDocs/prod/PTOInfo/pto_term_ sexpain.asp: printed on Feb. 4, 2004.

"Pain Disorders in Women" at http://www.burnc.bu.edu/Departments/PageMain.asp?Page=6930&DepartmentID=371; printed on Feb. 4, 2004.

"Sexual pain disorders" in Conditions & Treatments—Female Sexual Medicine at http://www.urology.medsch.ucla.edu/fsmc new-site-cond-sexpain.htm; printed on Feb. 4, 2004.

Baggish, M. S. and J. R. Miklos: "Vulvar pain syndrome: A review"; *Obstetrical and Gynecological Survey*; vol. 50, No. 8; pp. 618-627 (1995).

Butcher, J. "A psychosexual approach to managing dyspareunia"; *The Practitioner*; vol. 247, pp. 484-495; (Jun. 2003).

Glazer, H.: "Vulvovaginal pain disorders and sexual functioning" at http:www.selfhelpmagazine.com/articles/sex/pain.html; printed on Feb. 4, 2004; (Nov. 3, 2000).

Metts, J. F.: "Vulvodynia and vulvar vestibulitis: Challenges in diagnosis and management";*Am. Fam. Physician*, vol. 59, No. 6; pp. 1547-1556; (Mar. 15, 1999).

Ridley, C.M.: "Vulvodynia"; *Dermatologic Clinics*, vol. 16, No. 4; pp. 775-778; (Oct. 1998).

Walsh, K. E. et al.: "Safety and efficacy of topical nitroglycerin for treatment of vulvar pain in women with vulvodynia: A pilot study"; *J.G.S.M.*; vol. 5, No. 4; pp. 1-7; (Jul./Aug. 2002).

Welsh, B. et al.: "Management of common vulval conditions"; *M.J.A.*; vol. 178; pp. 391-395; (Apr. 21, 2003).

* cited by examiner

FIG. 1

COMPOUNDS AND METHODS FOR THE TREATMENT OF UROGENITAL DISORDERS

CROSS-REFERENCES TO RELATED APPLICATIONS

The present application claims priority to U.S. Provisional Patent Application Nos. 60/273,901, filed Mar. 6, 2001, and 60/334,903, filed Oct. 24, 2001, the teachings of both of which are incorporated herein by reference for all purposes.

BACKGROUND OF THE INVENTION

Urogenital disorders affect a large number of women and can have profound effects on life quality. Although a number of treatments are available for some of the most serious gynecological and urinary tract diseases, many urogenital disorders are still poorly understood. As a consequence, treatments are often nonexistent, inefficient and/or invasive.

One example of a relatively rare, yet highly debilitating, urogenital disorder is vaginismus. Vaginismus results from the involuntary spasm of the pelvic muscles surrounding the outer third of the vagina, and interferes with a woman's ability to have a sexual relationship. This disorder is a major cause of unconsummated marriage, and can result in marked distress, interpersonal difficulty, and infertility. In addition, women suffering from vaginismus are sometimes unable to undergo a routine gynecological exam. Typical treatments of vaginismus include, for example, psychological therapy, Kegel exercises, and the use of a plastic dilator to progressively stretch the contracted muscles of the vagina. Although often effective, these treatments are time-consuming and cause high levels of anxiety.

Dyspareunia is also characterized by difficult or painful sexual intercourse, although, unlike with vaginismus, vaginal penetration is possible. Only symptomatic treatments, such as the use of lubricants, are typically employed.

Another poorly understood disorder is vulvodynia, which involves a number of syndromes, including vulvar vestibulitis, which is characterized by pain in the vulvar area. Women with vulvodynia may even experience discomfort from clothing such as tight jeans. Furthermore, vulvodynia also affects a woman's ability to have sexual intercourse. To date, only treatments that alleviate the symptoms of vulvodynia are available.

Interstitial cystitis is a complex, chronic disorder characterized by an inflamed or irritated bladder wall. An estimated 700,000 people have interstitial cystitis, and about 90 percent of them are women. Interstitial cystitis can severely affect life quality, as patients suffer from bladder pain, frequency and/or urgency of urination. People with severe cases of interstitial cystitis may urinate as many as 60 times a day. Also, people with interstitial cystitis often experience pain during sexual intercourse. Only treatments that alleviate the symptoms of interstitial cystitis are available. These treatments are often ineffective, invasive and recurrence of the symptoms is frequently observed.

Female sexual arousal disorder (FSAD) is the persistent and recurring inability to attain or maintain sufficient sexual excitement, or a lack of genital lubrication, swelling or other somatic response (Berman, et al., "Anatomy and Physiology of Female Sexual Function and Dysfunction," Eur. Urol., 2000, 38:20–29). FSAD has been reported to have an overall prevalence of 14% in U.S. (Laumann, et al., Sexual Function in U.S., JAMA, 281:537–544 (1999)). Symptoms commonly associated with FSAD include: lack of or diminished vaginal lubrication, decreased clitoral and labial sensation and engorgement, and lack of vaginal smooth muscle relaxation. FSAD can occur secondarily to psychological disorders, but often is associated with medical or physiological changes. Currently, the only approved treatment for FSAD is a device called EORS, a vacuum pump device that induces clitoral engorgement. Sildenafil (i.e., Viagra®) has demonstrated efficacy in women with spinal cord injury, and in women using antidepressants such as serotonin reuptake inhibitors. However, it failed to show efficacy in a larger clinical trial including other patients suffering from FSAD. Phentolamine and testosterone have been used to treat FSAD, but these treatments may not effectively treat all of the symptoms associated with FSAD, and can be accompanied by significant side effects. An effective medical treatment is in need to treat this highly prevalent disorder.

Female sexual orgasmic disorder (FSOD) is defined as the persistent and recurrent difficulty, delay in or absence of attaining orgasm following sufficient sexual stimulation and arousal, and which causes personal distress. An effective medical treatment is in need to treat this highly prevalent disorder.

In view of the foregoing, it is readily apparent that there is a largely unmet medical need for effective, noninvasive and safe treatments of a large number of urogenital disorders including, but not limited to, vaginismus, dyspareunia, vulvodynia (including vulvar vestibulitis), interstitial cystitis, nonspecific urethritis (i.e., nonspecific pain and/or burning of the urinary tract), and sexual dysfunctions including, but not limited to, female sexual arousal disorders and female sexual orgasmic disorders. The present invention addresses these and other needs.

SUMMARY OF THE INVENTION

The present invention is based on the discovery that compounds such as NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators (including ATP-sensitive potassium channel activators and activators of the Maxi-K channels), estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators, endothelin receptor antagonists, bisphosphonates, cGMP-dependent protein kinase activators (e.g., cGMP mimetics), either alone or in combination, are effective for treating a variety of urogenital disorders including, but not limited to, vaginismus, dyspareunia, vulvodynia (including vulvar vestibulitis), interstitial cystitis, nonspecific urethritis (i.e., nonspecific pain and/or burning of the urinary tract), and a variety of sexual dysfunctions including, but not limited to, female sexual arousal disorders and female sexual orgasmic disorders.

In one aspect, the present invention provides a method for treating urogenital disorders, the method comprising administering to a patient in need thereof a compound selected from the group consisting of NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators, endothelin receptor antagonists, bisphosphonates, cGMP-dependent protein kinase activators (e.g., cGMP mimetics). In one embodiment, the urogenital disorder is selected from the group consisting of vaginismus, dyspareunia, vulvodynia (including vulvar vestibulitis), interstitial cystitis, nonspecific urethritis (i.e., nonspecific pain and/or burning of the urinary tract). In another embodiment, at least two different compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). The compound(s) may be administered via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and mucous membranes, the compound may be formulated as a gel, ointment, cream, lotion, powder, solution, suspension, spray, paste, oil, or foam. In some embodiments, the compound is administered by installation into the bladder. In yet other embodiments, plastic dilators of the type used to progressively stretch the contracted muscles of the vagina can be impregnated with the compound to deliver the compound topically to the vagina while stretching the vaginal muscles. In other embodiments, the compound is delivered continuously. For continuous delivery, a vaginal suppository, a cervical ring or an intrauterine device or a ring impregnated with the compound is inserted at the affected site.

In a second aspect, the present invention provides a method for treating vaginismus, the method comprising administering to a patient in need thereof a compound selected from the group consisting of calcium channel blockers, cholinergic modulators, α-adrenergic receptor antagonists, β-adrenergic receptor agonists, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators and adenylyl cyclase activators. In another embodiment, at least two different compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In another embodiment, the method further comprises administering to the patient a second compound selected from the group consisting of NO donors, phosphodiesterase inhibitors, cGMP-dependent protein kinase activators (e.g., cGMP mimetics). The compound may be administered via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and/or mucous membranes, the compounds may be formulated as a gel, ointment, cream, lotion, powder, solution, suspension, spray, paste, oil, or foam. Plastic dilators of the type used to progressively stretch the contracted muscles of the vagina impregnated with the compound can be used to deliver the compound topically to the vagina while simultaneously stretching the vaginal muscles. The compound may also be delivered continuously via a vaginal suppository, a cervical ring, or an intrauterine device or a ring inserted at the affected site.

In another aspect, the present invention provides a method for treating dyspareunia, the method comprising administering to a patient in need thereof a compound selected from the group consisting of cholinergic modulators, α-adrenergic receptor antagonists, cAMP-dependent protein kinase activators (e.g., cAMP mimetics), superoxide scavengers, potassium channel activators, testosterone-like compounds, benzodiazepines, adrenergic nerve inhibitors, antidiarrheal agents, HMG-CoA reductase inhibitors, smooth muscle relaxants, adenosine receptor modulators and adenylyl cyclase activators. In one embodiment, at least two compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In another embodiment, the method further comprises administering to the patient a second compound selected from the group consisting of NO donors, phosphodiesterase inhibitors, β-adrenergic receptor antagonists, estrogen-like compounds, cGMP-dependent protein kinase activators (e.g., cGMP mimetics). Again, the compounds may be administered via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. In one embodiment, the compounds are administered topically to the skin and/or mucous membranes and are in a form selected from the group consisting of gel, ointment, cream, lotion, powder, solution, suspension, spray, paste, oil, and foam. In another embodiment, the compound is delivered continuously by inserting at the affected site a vaginal suppository, a cervical ring, or an intrauterine device or a ring impregnated with the compound.

In yet another aspect, the present invention is directed to a method for treating interstitial cystitis, the method comprising administering to a patient in need thereof a compound selected from the group consisting of NO donors, β-adrenergic receptor agonists, phosphodiesterase inhibitors, cAMP-dependent protein kinase activators (e.g., cAMP mimetics), superoxide scavengers, potassium channel activators, testosterone-like compounds, benzodiazepines, antidiarrheal agents, HMG-CoA reductase inhibitors, smooth muscle relaxants, adenosine receptor modulators, adenylyl cyclase activators and endothelin receptor antagonists. In one embodiment, the method comprises administering to the patient at least two compounds selected from the foregoing list of compounds. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In another embodiment, the method further comprises administering to the patient a second compound selected from the group consisting of calcium channel blockers, cholinergic modulators, α-adrenergic receptor antagonists, estrogen-like compounds, adrenergic nerve inhibitors, cGMP-dependent protein kinase activators (e.g., cGMP mimetics). In particular embodiments, the compounds are administered via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and/or mucous membranes, the compounds are preferably in a form selected from the group consisting of gel, ointment, cream, lotion, powder, solution, suspension, spray, paste, oil, and foam. In a preferred embodiment, the compound is administered by installation into the bladder. In other embodiments, the compound is delivered continuously. For continuous delivery, a vaginal suppository, a cervical ring, or an intrauterine device or a ring impregnated with the compound is inserted at the affected site.

In still another aspect, a method for treating vulvodynia, including vulvar vestibulitis, is provided herein, the method comprising administering to a patient in need thereof a compound selected from the group consisting of NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators and bisphosphonates. Again, the compounds may be administered alone or in combination. In one embodiment, at least two compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In another embodiment, the method further comprises administering to the patient a second compound selected from the group consisting of cGMP-dependent protein kinase activators (e.g., cGMP mimetics). Administration may be via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and/or mucous membranes, the compounds may be formulated as a gel, ointment, cream, lotion, powder, solution, suspension, spray, paste, oil, or foam. Administration can also be by continuous delivery. For continuous delivery, a vaginal suppository, a cervical ring or an intrauterine device or a ring impregnated with said compound is inserted at the affected site.

In still another aspect, a method for treating vulvar vestibulitis, is provided herein, the method comprising administering to a patient in need thereof a compound selected from the group consisting of NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators and bisphosphonates. Again, the compounds may be administered alone or in combination. In one embodiment, at least two compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In another embodiment, the method further comprises administering to the patient a second compound selected from the group consisting of cGMP-dependent protein kinase activators (e.g., cGMP mimetics). Administration may be via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and/or mucous membranes, the compounds may be formulated as a gel, ointment, cream, lotion, powder, solution, suspension, spray, paste, oil, or foam. Administration can also be by continuous delivery. For continuous delivery, a vaginal suppository, a cervical ring or an intrauterine device or a ring impregnated with the compound is inserted at the affected site.

In still another aspect, a method for treating nonspecific urethritis (i.e., nonspecific pain, itching or burning of the urinary tract), is provided herein, the method comprising administering to a patient in need thereof a compound selected from the group consisting of NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators, endothelin receptor antagonists and bisphosphonates. Again, the compounds may be administered alone or in combination. In one embodiment, at least two compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In another embodiment, the method further comprises administering to the patient a second compound selected from the group consisting of cGMP-dependent protein kinase activators (e.g., cGMP mimetics). In another embodiment, the method further comprises administering an anti-microbial agent to the patient. In a preferred embodiment, the anti-microbial agent is effective against microorganisms such as gonorrhea, chlamydeous, etc. Administration may be via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and/or mucous membranes, the compounds may be formulated as a gel, ointment, cream, lotion, powder, solution, suspension, spray, paste, oil, or foam. In a preferred embodiment, the compound is administered by installation into the bladder. Administration can also be by continuous delivery. For continuous delivery, a vaginal suppository, a cervical ring or an intrauterine device or a ring impregnated with the compound is inserted at the affected site.

In still another aspect, a method for treating female sexual arousal disorders, is provided herein, the method comprising administering to a patient in need thereof a compound selected from the group consisting of NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, benzodiazepines, adrenergic nerve inhibitors, antidiarrheal agents, HMG-CoA reductase inhibitors, smooth muscle relaxants, adenosine receptor modulators, and adenylyl cyclase activators. Again, the compounds may be administered alone or in combination. In one embodiment, at least two compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In another embodiment, the method further comprises administering to the patient a second compound selected from the group consisting of testosterone-like compounds, prostaglandin-$E_1$, cGMP-dependent protein kinase activators (e.g., cGMP mimetics). Administration may be via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and/or mucous membranes, the compounds may be formulated as a gel, ointment, cream, lotion, powder, solution, suspension, spray, paste, oil, or foam. Administration can also be by continuous delivery. For continuous delivery, a vaginal suppository, a cervical ring or an intrauterine device or a ring impregnated with the compound is inserted at the affected site.

In still another aspect, a method for treating female sexual orgasmic disorders, is provided herein, the method comprising administering to a patient in need thereof a compound selected from the group consisting of NO donors, calcium channel blockers, cholinergic modulators, a-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, benzodiazepines, adrenergic nerve inhibitors, antidiarrheal agents, HMG-CoA reductase inhibitors, smooth muscle relaxants, adenosine receptor modulators and adenylyl cyclase activators. Again, the compounds may be administered alone or in combination. In one embodiment, at least two compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In another embodiment, the method further comprises administering to the patient a second compound selected from the group consisting of testosterone-like compounds, prostaglandin-$E_1$, cGMP-dependent protein kinase activators (e.g., cGMP mimetics). Administration may be via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and/or mucous membranes, the compounds may be formulated as a gel, ointment, cream, lotion, powder, solution, suspension, spray, paste, oil, or foam. Administration can also be by continuous delivery. For continuous delivery, a vaginal suppository, a cervical ring or an intrauterine device or a ring impregnated with the compound is inserted at the affected site.

In still another aspect, a method for facilitating a gynecological procedure is provided, the method comprising administering to a patient in need thereof a compound selected from the group consisting of NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators and cGMP-dependent protein kinase activators (e.g. cGMP mimetics). In some embodiment, at least two compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In one embodiment, the gynecological procedure is a gynecological exam. In another embodiment, the gynecological procedure is a gynecological surgery. In one embodiment, the compound reduces the pain or discomfort associated with the gynecological procedure. Administration may be via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and/or mucous membranes, the compounds may be formulated as a gel, ointment, cream, lotion, powder, solution, suspension, spray, paste, oil, or foam. Administration can also be by continuous delivery. For continuous delivery, a vaginal suppository, a cervical ring or an intrauterine device or a ring impregnated with the compound is inserted at the affected site.

In still another aspect, a method for increasing a condition selected from the group consisting of vaginal lubrication, clitoral or labial sensitivity and engorgement and relaxation of vaginal smooth muscle is provided, the method comprising administering to a patient in need thereof a compound selected from the group consisting of NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, and adenylyl cyclase activators. In some embodiment, at least two compounds selected from the foregoing list of compounds are administered to the patient. In some embodiments, the at least two compounds are selected from the same class of compounds (e.g., both compounds are phosphodiesterase inhibitors), whereas in other embodiments, the at least two compounds are selected from different classes of compounds (e.g., one compound is a phosphodiesterase inhibitor and the other compound is an NO donor). In other embodiments, the method further comprises administering to the patient a second compound selected from the group consisting of cGMP-dependent protein kinase activators (e.g., cGMP mimetics). Administration may be via the oral, parenteral (intravenous, intramuscular or subcutaneous), transdermal, transurethral (or intraurethral), pulmonary or transmucosal (nasal, buccal, cervical, vaginal, anorectal) route for systemic and/or local delivery. For topical administration to the skin and/or mucous membranes, the compounds may be formulated as a gel, ointment, cream, lotion, powder, solution, suspension, spray, paste, oil, or foam. Administration can also be by continuous delivery. For continuous delivery, a vaginal suppository, a cervical ring or an intrauterine device or a ring impregnated with the compound is inserted at the affected site.

In still another aspect, pharmaceutical kits comprising one or more containers filled with one or more of the ingredients of the pharmaceutical compounds and/or compositions of the present invention are provided herein. Such kits can also include, for example, other compounds and/or compositions (e.g., permeation enhancers, lubricants, etc.), a device(s) for administering the compound and/or compositions, and written instructions in a form prescribed by a government agency regulating the manufacture, use or sale of pharmaceuticals, medical devices or biological products, which instructions can also reflect approval by the agency of manufacture, use or sale for human administration.

DETAILED DESCRIPTION OF THE INVENTION

Figure 1:
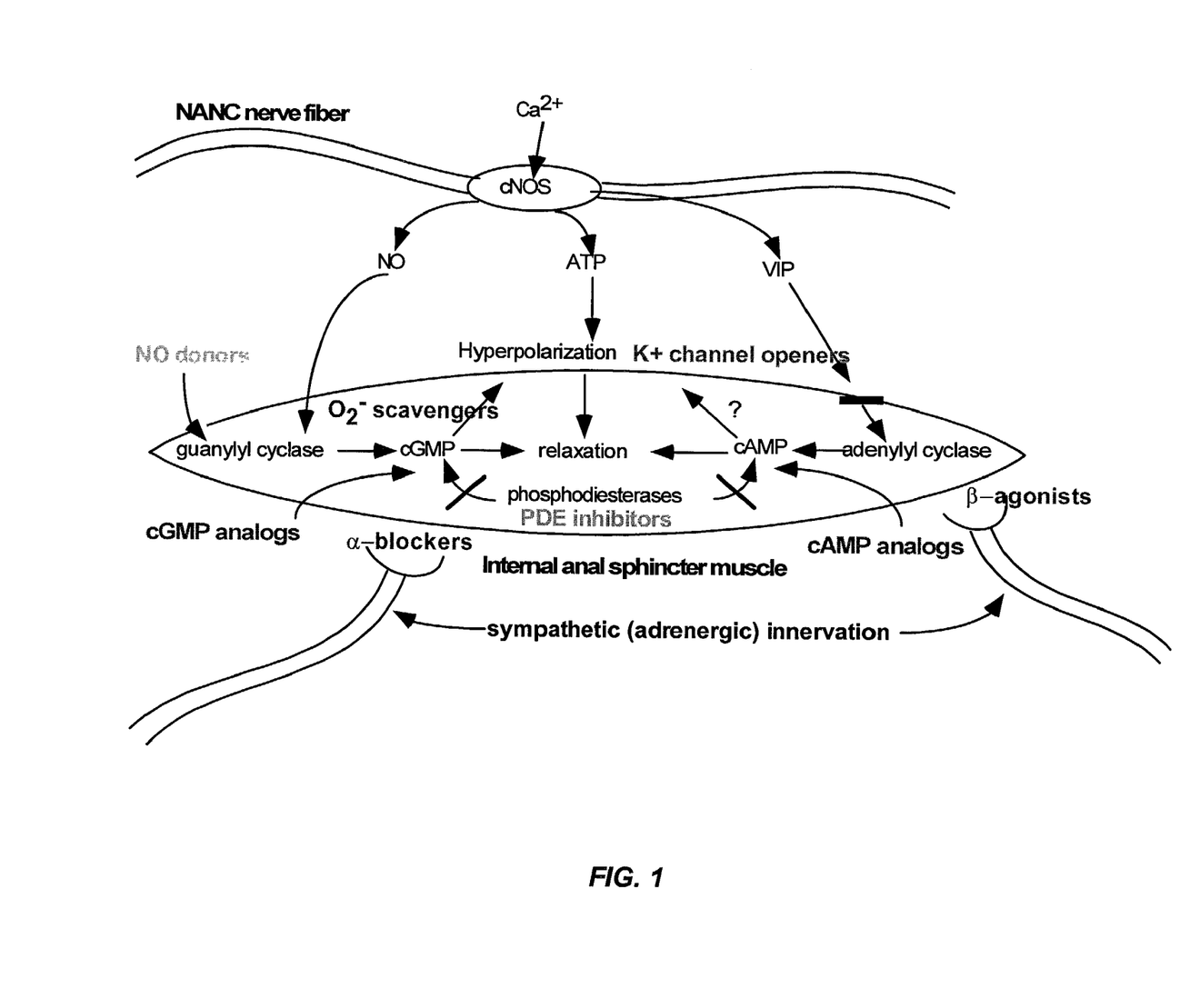
FIG. 1 illustrates compounds useful in the methods and compositions of the present invention.

The present invention provides novel, noninvasive methods for treating urogenital disorders using nitric oxide (NO) donors and other agents that either interfere with the downstream biochemical events leading to smooth muscle relaxation, or block signals for smooth muscle contraction. The present invention also provides novel, noninvasive methods for treating urogenital disorders in men and women using NO donors and other agents that interfere with the downstream biochemical events leading to suppression of pain and discomfort due to infections, inflammation or nonspecific nociceptive activation. Such compounds are effective for treating a variety of urogenital disorders including, but not limited to, vaginismus, dyspareunia, vulvodynia (including vulvar vestibulitis), interstitial cystitis, nonspecific urethritis (i.e., nonspecific pain and/or burning of the urinary tract) and sexual dysfunctions including, but not limited to, female sexual arousal disorders and female sexual orgasmic disorders. Suitable compounds for use with the methods of the present invention are described infra and include, in particular, NO donors, calcium channel blockers, cholinergic modulators (including acetylcholine storage blocking agents and acetylcholine vesicle transport blocking agents), $\alpha$-adrenergic receptor antagonists (including $\alpha_1$-adrenergic receptor antagonists and $\alpha_2$-adrenergic receptor antagonists), $\beta$-adrenergic receptor agonists (including $\beta_2$-adrenergic receptor agonists and $\beta_3$-adrenergic receptor agonists), phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators, endothelin receptor antagonists, bisphosphonates, cGMP-dependent protein kinase activators (e.g., cGMP mimetics). These compounds may be administered in stand-alone therapy, in combination therapy or as separate dosage forms administered simultaneously or in succession.

The compounds of the present invention may be administered therapeutically to a patient affected with one or more of the above-listed disorders, as well as prior to urological or gynecological examination. Administration can be via the oral, parenteral (intravenous, intramuscular or subcutaneous), transdermal, transurethral (or intraurethral), pulmonary or transmucosal (nasal, buccal, cervical, vaginal, anorectal) route, for systemic and/or local delivery, with local delivery being preferred. Administration can also be by installation into the bladder. To provide pharmacological therapy in conjunction with traditional muscle stretch therapy used to treat vaginismus, plastic dilators impregnated with the compound may be used to deliver the compound topically to the vagina while simultaneously stretching the vaginal muscles. To prevent the relapse or to treat a chronic condition, a vaginal suppository, a cervical ring, or an intrauterine device or ring impregnated with one or more of the compounds described herein can be inserted at the affected site to provide continuous delivery.

I. Urogenital Disorders

In the context of the present invention, the term "urogenital disorder" encompasses any disease or disorder in a patient that affects the urogenital tract. Urogenital disorders can occur in men, women and other mammals, can be idiopathic or can arise due to a number of factors including infection, inflammation, surgery, circumcision, trauma, such as childbirth, pelvic and perineal injuries, etc., acute or chronic illnesses, such as diabetes, cardiovascular disorders, cancers, etc., chemotherapy, radiation therapy or genital mutilation. A number of urogenital conditions and diseases can lead to subsequent female sexual dysfunction.

Female sexual dysfunction refers to any disorder affecting sexual intercourse, including sexual pain disorders, impossible intercourse, dyspareunia, vaginismus, arousal disorders, etc. Sexual dysfunction can be caused by a variety of factors, including but not limited to, menopause, pregnancy, aftermath of childbirth, cancer, surgery, radiation therapy, chronic medical illness or medications. One of the benefits of the methods of the present invention is that they treat the underlying urogenital disorder, thereby treating the resulting sexual dysfunction. The patient is preferably a mammal and most preferably a human.

A. Vaginismus

Vaginismus is a relatively rare, but highly debilitating, urogenital disorder. Vaginismus can be defined as a recurrent or persistent involuntary spasm of the musculature of the lower third of the vagina that surrounds the vaginal opening. This muscular contraction makes any attempt at vaginal penetration either extremely painful or impossible (for further information see, e.g., The Human Sexuality Web, http:// www.umkc.edu/sites/hsw/issues/vaginis.html), and it may also affect a woman's ability to undergo a routine gynecological exam or to use tampons. Vaginismus may have both physical and psychological causes. Vaginismus is most commonly treated with progressive vaginal dilation, if necessary, along with counseling or couples therapy. Progressive vaginal dilation involves the use of vaginal inserts, each progressively larger than the last, which help condition the vaginal opening. As one becomes comfortable, the next larger size is inserted in the vagina and worn until it is comfortable. This continues until the vagina has been dilated sufficiently for intercourse to take place painlessly.

B. Dyspareunia

Dyspareunia is a disorder characterized by difficult or painful sexual intercourse. With dyspareunia, unlike vaginismus, vaginal penetration is possible, but is usually very uncomfortable. Dyspareunia may be caused by a number of physical factors such as, for example, tension, thinning of the labia as a woman ages, inadequate lubrication, gynecological conditions such as endometriosis, fibroid or other uterine tumors, infection of the genitals, pressure against the vaginal wall caused by scarring from operations or radiation treatment, allergic reactions, the aftermath of childbirth, etc. In some cases, dyspareunia may be caused by a number of psychological factors, and fatigue, overwork, stress, recent illness, and alcohol consumption may increase the symptoms. For further information see, e.g., http://www.dyspareunia.org/.

Typical symptomatic treatments of dyspareunia include, for example, the use of lubricants such as egg white, K-Y surgical lubrication jelly, Astroglide®, Replens®, etc. (see, e.g., Semmens, *Medical Aspects of Human Sexuality*, 8:85–86 (1974); and Frishmen, et al., *Fertility and Sterility*, 58:630 (1992)). When symptomatic treatment fails, pharmacological treatment may be indicated (see, e.g., Nadelson, et al. (eds.) *Treatment Interventions in Human Sexuality*, Plenum Press, NY (1983)).

C. Interstitial Cystitis

Interstitial cystitis (IC) is a disorder associated with chronic inflammation of the bladder wall and primarily manifested by bladder pain and irritative voiding (i.e., day and/or night frequency of urination). Additional symptoms include, but are not limited to, urgency, sometimes accompanied by pain, pressure or spasms, lower abdominal, urethral or vaginal pain, as well as pain associated with sexual intercourse. Unlike common cystitis, which is caused by bacteria and is usually successfully treated with antibiotics, the causes of interstitial cystitis are unknown and IC does not respond to conventional antibiotic therapy. Although IC can affect people of any age, race or sex, it is most commonly found in women. For further information see, e.g., Interstitial Cystitis Association, http://www.ichelp.org/.

At this time there is no cure for IC, nor is there an effective treatment which works for everyone. A number of treatments appear to alleviate the symptoms of IC, including, but not limited to, oral administration of ELMIRON® (pentosan polysulfate sodium), anti-inflammatory agents, antispasmodics, antihistamines, muscle relaxants, and tricyclic antidepressants such as Elavil® (amitriptyline), bladder distention, direct instillation into the bladder of DMSO (dimethyl sulfoxide), CYSTISTAT® (hyaluronic acid), heparin, silver nitrate, or Clorpactin® (oxychlorosene sodium), Transcutaneous Electrical Nerve Stimulation, and a number of surgical procedures. These treatments do not always work, are associated with a number of side effects, and are often invasive. Furthermore, even when symptoms disappear, recurrence is frequently observed.

D. Vulvodynia

Vulvodynia refers to a number of syndromes characterized by vulvar pain. Typically, the vulva is so sensitive that even light pressure can be painful. The entire vulva or only a portion of the vulva surrounding the entry to the vagina (i.e., the vestibule) may be involved. Women with vulvodynia may experience rashes or scaly patches on the vulva with visible areas of redness or irritation, but may also not have any physical abnormalities of the vagina. Additional symptoms associated with vulvodynia include, but are not limited to, painful penetration, recurrent, intractable vaginal infections, vaginal secretions, dryness, inability to tolerate speculum exams, swollen feeling, pelvic floor spasms, decreased sex drive, dysmenorrhea, etc. The condition varies in persistence and location, and pain may be constant or intermittent, localized or diffuse.

The exact causes of vulvodynia are unknown, although it has been suggested that neurological injury, skin conditions or dermatoses may be involved in some types of vulvodynia. External causes including, for example, previous treatments such as laser surgery, or sensitivity to corticosteroid drugs may also play a role.

There are several subcategories of vulvodynia, including periorificial dermatitis or vulvar dermatoses (skin condition involved), pudendal neuralgia or dysthetic vulvodynia (nerve injury involved), vulvar vestibulitis (only the area around the opening to the vagina, or vestibule, is involved) and cyclic vulvovaginitis (*Candida* yeast involved). For further information on vulvodynia see, e.g., National Vulvodynia Association http://www.nva.org/, Interstitial Cystitis Association, http://www.ichelp.org/.

Currently, there is no cure for vulvodynia. Treatments directed toward symptom relief include, for example, drug therapies such as tricyclic antidepressants or anticonvulsants, nerve blocks, interferon, biofeedback, diet modification, and in some cases surgical intervention.

E. Nonspecific Urethritis

Nonspecific urethritis (i.e., nonspecific pain, itching or burning of the urinary tract) is a syndrome of unknown etiology that occurs most often in women. Upon medical examination, these women have no previous history of pelvic floor surgery, no interstitial cystitis and no signs of infection or inflammation. However, pain, itching and/or burning occurs during urination, but the pain, itching or burning sensation is not necessarily limited to urination. Currently, there is no effective medical therapy for treating this disorder.

F. Female Sexual Arousal Disorders

The female sexual response is a complex and integrated process involving multiple factors, including both CNS-stimulated and peripherally-stimulated, neurotransmitter-mediated vascular and smooth muscle relaxation, which results in increased vaginal lubrication, vaginal wall engorgement, and increased luminal volume, and clitoral length and size. The cascade of events surrounding female sexual arousal is intimately connected with, among other factors, relationship issues, psychological and socioeconomic status, other medical conditions, and the patient's own sense of well being.

Female sexual arousal disorder (FSAD) is defined as the persistent and recurring inability to attain or maintain sufficient sexual excitement, which causes personal distress. It may be experienced as a lack of subjective excitement or as the lack of genital lubrication, swelling or other somatic response (Berman, et al., Anatomy and Physiology of Female Sexual Function and Dysfunction, Eur. Urol., 38:20–29 (2000)). The symptoms of FSAD include, but are not limited to, lack of or diminished vaginal lubrication, decreased clitoral and labial sensation and engorgement, and lack of vaginal smooth muscle relaxation. These conditions can occur secondarily to psychological disorders, but often are associated with medical or physiological changes.

G. Female Sexual Orgasmic Disorders

Female sexual orgasmic disorder is defined as the persistent and recurrent difficulty, delay in or absence of attaining orgasm following sufficient sexual stimulation and arousal, and which causes personal distress.

II. Compounds of the Invention

The present invention provides methods for treating the urogenital disorders described supra. Suitable compounds for use with the methods of the present invention are well known in the art and are described, e.g., in Goodman and Gilman, *The Pharmacological Basis of Therapeutics* (9th Ed.), McGraw-Hill, Inc. (1996); *The Merck Index* (12th Ed.), Merck & Co., Inc. (1996); *The Physician's Desk Reference* (49th Ed.), Medical Economics (1995); and *Drug Facts and Comparisons*, Facts and Comparisons (1993).

A. NO Donors

In preferred embodiments, the compounds of the present invention are NO donors. The nitric oxide donor can be any of a variety of NO donors including, for example, organic NO donors, inorganic NO donors and prodrug forms of NO donors. Additional suitable NO donors include compounds that can be metabolized in vivo into a compound which delivers nitric oxide (e.g., a prodrug form of a NO donor, or a binary NO generating system, such as acidified nitrates), or compounds that serve as physiological precursor of nitric oxide, such as L-arginine and salts of L-arginine. The NO donor may include at least one organic nitrate (including esters of nitric acid) and can be either a cyclic or acyclic compound. For example, suitable NO donors include nitroglycerin (NTG), isosorbide dinitrate (ISDN), isosorbide mononitrate (ISMN) which may include isosorbide-2-mononitrate (IS2N) and/or isosorbide-5-mononitrate (IS5N), erythrityl tetranitrate (ETN), pentaerythritol tetranitrate (PETN), ethylene glycol dinitrate, isopropyl nitrate, glyceryl-1-mononitrate, glyceryl-1,2-dinitrate, glyceryl-1,3-dinitrate, butane-1,2,4-triol trinitrate, and the like. Nitroglycerin and other organic nitrates including ISDN, ETN, and PETN, have been given regulatory approval for use in treatments in other fields of medicine on human subjects. Additional NO donors include sodium nitroprusside, N,O-diacetyl-N-hydroxy-4-chlorobenzenesulfonamide, $N^G$-hydroxy-L-arginine (NOHA), hydroxyguanidine sulfate, molsidomine, 3-morpholinosydnonimine (SIN-1), (±)-S-nitroso-N-acetylpenicillamine (SNAP), S-nitrosoglutathione (GSNO), (±)-(E)-ethyl-2-[(E)-hydroxyimino]-5-nitro-3-hexeneamide (FK409), (±)-N-[(E)-4-ethyl-3-[(Z)-hydroxyimino]-5-nitro-3-hexen-1-yl]-3-pyridinecarboxamide (FR144420), and 4-hydroxymethyl-3-furoxancarboxamide. In addition, compounds that interfere with the breakdown of NO in vivo may be administered.

B. Calcium Channel Blockers $Ca^{2+}$ channel blockers are compounds that inhibit the entry of $Ca^{2+}$ into the cell from the extracellular fluid. Suitable $Ca^{2+}$ channel blockers for use with the methods of the present invention include, but are not limited to, nifedipine, nimodipine, felopidine, nicardipine, isradipine, amlodipine, diltiazem, bepridil, verapamil, etc. (see, e.g., WO 98/36733). L-type $Ca^{2+}$ channel blockers are also available C. Cholinergic Modulators Other preferred compounds for use in the context of the present invention include cholinergic modulators (see, e.g., WO 98/36733). Cholinergic modulators suitable for use with the methods of the present invention include, but are not limited to, ambenonium, bethanechol, cisapride, edrophonium, neostigmine, physostigmine, pilocarpine, pyridostigmine, succinylcholine, tacrine, etc. Compounds (e.g., Botulinium Toxin) that can terminate the release of neurotransmitters (e.g., acetylcholine) are also suitable for use in the methods of the present invention. Acetylcholine storage blocking agents and acetylcholine vesicle transport blocking agents, such as vesamicol, are also preferred. Vesamicol prevents the storage of acetylcholine in the presynaptic storage vesicles as well as the release and transport of acetylcholine from these vesicles.

A. α-Adrenergic Receptor Antagonists and β-Adrenergic Receptor Agonists

Additional preferred compounds for use in the context of the present invention include, e.g., α-adrenergic receptor antagonists and β-adrenergic receptor agonists. Suitable α-adrenergic receptor antagonists include, for example, $α_1$-adrenergic receptor antagonists, $α_2$-adrenergic receptor antagonists and other nonspecific α-adrenergic receptor antagonists. Preferred $α_1$-adrenergic receptor antagonists include, but are not limited to, prazosin, doxazosin, phenoxybenzamine, phentolamine, terazosin, tolazoline, etc., and are described in Goodman and Gilman, "*The Pharmaceutical Basis of Therapeutics,*" 9th Edition, Hardman, et al. (ed.), McGraw-Hill (1996). Suitable $α_2$-adrenergic receptor antagonists include, but are not limited to, yohimbine and are also described in Goodman and Gilman, "*The Pharmaceutical Basis of Therapeutics,*" 9th Edition, Hardman, et al. (ed.), McGraw-Hill (1996). Other suitable antagonists are $α_2$-adrenergic antagonists include, for example, post-synaptic $α_2$-adrenergic antagonists. These post-synaptic $α_2$-adrenergic antagonists include, but are not limited to, imiloxan, ARC 239 dihydrochloride and other pharmaceutically acceptable salts thereof. ARC 239 dihydrochloride is 2-[2-(4-(2-Methoxyphenyl)piperazin- 1-yl)ethyl]-4,4-dimethyl-1,3-(2H,4H)-isoquinolindone dihydrochloride. Other suitable post-synaptic $α_2$-adrenergic antagonists include, but are not limited to, idazoxan, rauwolscine, efaroxan, mianserin, and mirtazapine. Of these, mianserin and mirtazapine are particularly preferred.

Suitable β-adrenergic receptor agonists for use with the methods of the present invention include, but are not limited to, $β_1$-adrenergic receptor agonists, $β_2$-adrenergic receptor agonists, $β_3$-adrenergic receptor agonists and other nonspecific β-adrenergic receptor agonists. In a preferred embodiment, the β-adrenergic receptor agonist is a $β_2$-adrenergic receptor agonist or a $β_3$-adrenergic receptor agonists. Examples of β-adrenergic receptor agonists suitable for use with the methods of the present invention include, but are not limited to, albuterol, bitolterol, salbutamol, terbutaline, metaproterenol, procaterol, salmeterol, clenbuterol, isoproterenol, zinterol, BRL 37344, CL316243, CGP-12177A, GS 332, L-757793, L-760087, L-764646, and L-766892, etc. (see, e.g., Goodman and Gilman, supra).

E. Phosphodiesterase Inhibitors

In another preferred embodiment, the compound is a phosphodiesterase inhibitor. Cyclic nucleotide second messengers (cAMP and cGMP) play a central role in signal transductions and regulation of physiologic responses. Their intracellular levels are controlled by the complex superfamily of cyclic nucleotide phosphodiesterases (PDE) enzymes. Inhibitors of phosphodiesterases (PDE) are agents that can either activate or suppress PDEs via allosteric interaction with the enzymes or binding to the active site of the enzymes. The PDE family includes at least 19 different genes and at least 11 PDE isozyme families, with over 50 isozymes having been identified thus far. The PDEs are distinguished by (a) substrate specificity, i.e., cGMP-specific, cAMP-specific or nonspecific PDEs, (b) tissue, cellular or even sub-cellular distribution, and (c) regulation by distinct allosteric activators or inhibitors. PDE inhibitors include both nonspecific PDE inhibitors and specific PDE inhibitors (those that inhibit a single type of phosphodiesterase with little, if any, effect on any other type of phosphodiesterase). Still other useful PDE inhibitors are the dual selective PDE inhibitors (e.g., PDE III/IV inhibitors or PDE II/IV inhibitors). Below is a table setting forth various PDE inhibitors that are useful in the methods of the present invention.

| Isozyme Family | Regulatory Characteristics | Selective Inhibitors |
|---|---|---|
| I | $Ca^{2+}$, Calmodulin-regulated with different $K_m$ values for cG and cA hydrolysis | Vinpocetine |
| III | CG-inhibited cA hydrolysis; low $K_m$ for cA and cG | Milrinone, Amrinone, Pimobendan, Cilostamide, Enoximone, Peroximone, Vesarinone |
| IV | Low $K_m$ for cA hydrolysis | Rolipram; RO-20-1724 |
| V | High and low Km isoforms for cG specific hydrolysis | Zaprinast; Dipyridamole |

In one embodiment, the PDE inhibitor is a PDE V inhibitor. Useful phosphodiesterase type V inhibitors include, e.g., cialis, tanadafil, zaprinast, MBCQ, MY-5445, dipyridamole and sildenafil. In another embodiment, the composition contains a phosphodiesterase type II (PDE II) inhibitor such as, e.g., EHNA. In yet another embodiment, the composition contains a phosphodiesterase type IV (PDE IV) inhibitor. Suitable phosphodiesterase type IV inhibitors include, but are not limited to, roflumilast, ariflo (SB207499), RP73401, CDP840, rolipram, RO-20-1724, and LAS31025. In still another embodiment, the phosphodiesterase inhibitor is a dual selective phosphodiesterase inhibitor such as, e.g., a PDE III/IV inhibitor (e.g., zardaverine).

In another embodiment, the PDE inhibitor is an inhibitor of the PDE IV isozyme family, or cAMP-specific and rolipram sensitive PDEs, which preferentially hydrolyze cAMP.

In yet another embodiment, the composition contains an agent that is a nonspecific phosphodiesterase inhibitor. Suitable nonspecific phosphodiesterase inhibitors include, but are not limited to, theobromine, dyphylline, IBMX, theophylline, aminophylline, pentoxifylline, papaverine, caffeine and other methylxanthine derivatives.

F. cAMP-dependent Protein Kinase Activators

In other preferred embodiments, the compound used to treat the disorders described herein is a cAMP-dependent protein kinase activator. Examples of cAMP-dependent protein kinase activators include cAMP mimetics or dual cGMP/cAMP-dependent protein kinase activators. Suitable cAMP mimetics or analogs include those compounds that are structurally similar to cAMP and that have similar functions e.g., activities, as cAMP. Examples of suitable cAMP mimetics include, but are not limited to, 8-bromo-cAMP, dibutyryl-cAMP, Rp-cAMPS, and Sp-cAMPS, and useful dual activators include compounds such as, e.g., Sp-8-pCPT-cGMPS, Sp-8-bromo-cGMPS and 8-CPT-cAMP.

G. Superoxide Scavengers

In another aspect, the compound used in the compositions and methods of the present invention is a superoxide anion ($O_2^-$) scavenger. Superoxide can react with NO and dramatically reduce its biological effects. Accordingly, agents that scavenge superoxide anions can enhance the effects of NO. Examples of superoxide scavengers include, but are not limited to, exogenous Mn or Cu/Zn superoxide dismutase (SOD) or small molecule SOD mimetics such as, e.g., Mn(III) tetra(4-benzoic acid) porphyrin chloride (MnTBAP) and M40403 (see, e.g., Salvemini, et al., *Science*, 286(5438): 304–306 (1999)).

H. Potassium Channel Activators

In another aspect, the present invention provides pharmaceutical compositions comprising a potassium channel activator. In one embodiment, the potassium channel activator is an ATP-sensitive potassium channel activator. Synthetic compounds that activate ATP-sensitive K channels are smooth muscle relaxants. Such compounds include, but are not limited to, minoxidil, minoxidil sulfate, pinocidil, diazoxide, levcromokalim, cromokalim, etc. (see, e.g., White, et al., *Eur. J. Pharmacol.*, 357:41–51 (1998)). Additional suitable ATP-sensitive K channel activators can be found in, e.g., Bristol, et al., "Annual Reports in Medicinal Chemistry," Vol. 29, Chap. 8, pp. 73–82, Academic Press (1991). In another embodiment, the potassium channel activator is a Maxi-K channel activator. Examples of activators of the Maxi-K channels include, but are not limited to, estrogen-like compounds, such as estradiol (see, Valverde, et al., *SCIENCE*, 285:1929–1931).

I. Estrogen-like Compounds

In another aspect, the present invention provides pharmaceutical compositions comprising an estrogen-like compound. Estrogen-like compounds include those compounds that bind to the estrogen receptor and act as agonists thereof. Estrogen-like compounds include, but are not limited to, 17-β-estradiol, estrone, mestranol, estradiol valerate, estradiol dypionate, ethynyl estrodil, quinestrol, estrone sulfate, phytoestrogens such as flavones, isoflavones (e.g., genistein), resveratrol, coumestan derivatives, other synthetic estrogenic compounds including pesticides (e.g., p,p'-DDT), plasticizers (e.g., bisphenol A), and a variety of other industrial chemicals (e.g., polychlorinated biphenyls) (see, e.g., Goodman and Gilman, supra).

J. Testosterone-like Compounds

In another aspect, the present invention provides pharmaceutical compositions comprising a testosterone-like compound. Testosterone-like compounds include those compounds that bind to the testosterone receptor and act as agonists thereof. Testosterone-like compounds include, but are not limited to, testosterone, testosterone propionate, testosterone enanthate, testosterone cypionate, testosterone undecenoate, dihydrotestosterone, danazol, fluoxymesterone, methyltestosterone, oxandrolone, DHEA and tibolone (see, e.g., Goodman and Gilman, supra).

K. Benzodiazepines

In another aspect, the present invention provides pharmaceutical compositions comprising a benzodiazepine. Suitable benzodiazepines include, but are not limited to, alprazolam, brotizolam, chlordiazepoxide, clobazam, clonazepam, chlorazepate, demoxepam, diazepam, estazolam, flumazenil, flurazepam, halazepam, lorazepam, midazolam, nitrazepam, nordazepam, oxazepam, prazepam, quazepam, temazepam, and triazolam (see, e.g., Goodman and Gilman, supra).

L. Adrenergic Nerve Inhibitors

In another aspect, the compounds of the present invention are compounds that inhibit adrenergic nerves. Adrenergic nerve inhibitors include compounds that destroy sympathetic nerve terminals, such as 6-hydroxydopamine and its analogs (see, e.g., Goodman and Gilman, supra). Adrenergic nerve inhibitors also include compounds that deplete norepinephrine storage, either by inhibiting norepinephrine biosynthesis or be depleting stores, and compounds that inhibit norepinephrine release. Compounds that inhibit norepinephrine biosynthesis include, but are not limited to, α-methyl-tyrosine. Compounds that deplete norepinephrine stores include, but are not limited to, reserpine, guanethidine and bretylium. Compounds that inhibit norepinephrine release include, but are not limited to, clonidine and other $\alpha_2$-adrenergic receptor antagonists. Examples of sympathetic nerve terminal destroyers include, but are not limited to, $\alpha_2$-adrenergic receptor antagonists.

M. Antidiarrheal Agents

In another aspect, the compounds of the present invention are antidiarrheal agents. Examples of suitable antidiarrheal agents include, but are not limited to, diphenoxylate, loperamide, bismuth subsalicylate, octreotide, etc. (see, e.g., Goodman and Gilman, supra).

N. HMG-CoA Reductase Inhibitors

In another aspect, the compounds of the present invention are HMG-CoA reductase inhibitors. Examples of HMG-CoA reductase inhibitors include, but are not limited to, mevastatin, lovastatin, simvastatin, pravastatin, cerivastatin, dalvastatin, atorvastatin, fluvastatin, etc. (see, e.g., Goodman and Gilman, supra).

O. Smooth Muscle Relaxants

In other embodiments, the compounds of the present invention are smooth muscle relaxants such as, e.g., hydralazine, papaverine, tiropramide, cyclandelate, isoxsuprine and nylidrin.

P. Adenosine Receptor Modulators

In another aspect, the present invention provides compositions for the treatment of urogenital tract disorders comprising adenosine receptor modulators, either alone or in combination with another agent. Methods for the use of these compositions are also provided. In one group of embodiments, adenosine receptor modulators are used alone. In another group of embodiments, the adenosine receptor modulators are combined with at least one other urogenital muscle-relaxing agent. In other embodiments, the compounds of the present invention are adenosine receptor modulators such as methylxanthines. Examples of adenosine receptor modulators include theophylline and dyphylline. For other examples see, Goodman & Gilman, supra). Preferred agents are selected from those described with reference to the compositions of single agents or combinations above.

Theophylline, a plant-derived methylxanthine, has been used for the treatment of bronchial asthma for decades. Theophylline relaxes smooth muscle, notably bronchial muscle, that has been contacted experimentally with a spasmogen, or clinically in asthma. Proposed mechanisms of methylxanthine-induced physiologic and pharmacological effects include: 1) inhibition of phosphodiesterases, thereby increasing intracellular cyclic AMP, 2) direct effects on intracellular calcium concentration, 3) indirect effects on intracellular calcium concentrations via cell membrane hyperpolarization, 4) uncoupling of intracellular calcium increases with muscle contractile elements, and 5) antagonism of adenosine receptors.

A related compound, i.e., dyphylline, is a preferred adenosine receptor modulator. This compound is not metabolized by the liver and is excreted unchanged by the kidneys, therefore its pharmacokinetics and plasma levels are independent of factors that effect liver enzymes such as smoking, age, congestive heart failure, or the use of other drugs that affect liver function.

Q. Adenylyl Cyclase Activators

In another aspect, the present invention provides compositions comprising adenylyl cyclase activators, either alone or in combination with other compounds or agents described herein. The adenylyl cyclase activator forskolin is preferred. Other examples of adenylyl cyclase activators, include, but are not limited to, N6, O2'-dibutyryl-cAMP, 8-chloro-cAMP, and Rp-diastereomers of adenosine 3',5'-cyclic monophosphorothioate, and related analogs, such as Rp-8-bromoadenosine 3', 5'-cyclic monophosphorothioate, and derivatives of forskolin, including colforsin daropate hydrochloride.

R. Endothelin Receptor Antagonists

In another aspect, the present invention provides compositions comprising endothelin receptor antagonist, either alone or in combination with other compounds disclosed herein. Examples of endothelin receptor antagonists include, but are not limited to, BE 1827B, JKC-301, JKC- 302, BQ-610, W-7338A, IRL-1038, LRL-1620, bosetan, ABT 627, Ro 48-5695, Ro 61-1790, tesosentan (Ro 61-0612, ZD1611, BMS-187308, BMS-182874, BMS-193884, sitaxsentan (TBC 11251), TBC 2576, TBC 3214, TBC-10950, ABT-627, atrasentan, A-192621, A-308165, A-216536, CI-1020, EMD 122946, J-234551, SB 247083, ATZ1993, PABSA, L-749,329, RPR111723, RPR11801A, PD 164800, PD 180988 (CI1034), IRL 3630, IRL 2500, and their derivatives, etc. (see, Doherty, Annual Reports in Medicinal Chemistry, Volume 35, pp. 73–82, Academic Press, 2000). Other ethenesulfonamide derivatives, which are endothelin receptor antagonists and which are useful in the methods of the present invention, are disclosed by Harada, et al., *Chem. Pharm. Bull.*, 49(12):1593–1603 (2001).

S. Bisphosphonates

In another aspect, the present invention provides compositions comprising bisphosphonates, either alone or in combination with other agents. Suitable bisphosphonates suitable for use in the methods of the present invention include, but are not limited to, alendronate sodium (Fosamax), pamidronate disodium (Aredia), etidronate disodium Ididronel) and the like.

T. cGMP-dependent Protein Kinase Activators

In another aspect, the present invention provides cGMP-dependent protein kinase activators, either alone or in combination with other agents disclosed herein. Suitable cGMP-dependent protein kinase activators include, but are not limited to, cGMP mimetics or dual cGMP/cAMP-dependent protein kinase activators. Suitable cGMP mimetics or analogs include those compounds that are structurally similar to C GMP and that have similar functions, e.g., activities, as CGMP. Examples of suitable cGMP mimetics include, but are not limited to, 8-bromo-cGMP, dibutyryl-cGMP, Rp-cGMPS, and Sp-cGMPS, and useful dual activators include compounds such as, e.g., Sp-8-pCPT-cGMPS, SP-8-bromo-cGMPS and 8-CPT-cAMP.

III. Pharmaceutical Compositions and Administration

The present invention also provides pharmaceutical compositions for the administration of the herein-described compounds, e.g., the NO donors, calcium channel blockers, cholinergic modulators, a-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators, endothelin receptor antagonists, bisphosphonates, cGMP-dependent protein kinase activators (e.g., cGMP mimetics), to a patient in need thereof. In the context of the present invention, the term "patient" refers to a subject to which the compounds of the invention can be administered. Preferably, a patient is a mammal, e.g., a rodent, a primate or a human. If the patient is a human, the human can be either male or female. A patient may be affected with a disease, or may be free of detectable disease in which case the compounds and compositions of the present invention are administered prophylactically. The compositions of the present invention can be administered to patients with a urogenital disorder such as, for example, vaginismus, dyspareunia, vulvodynia (including vulvar vestibulitis), interstitial cystitis, nonspecific urethriris (i.e., nonspecific pain and/or burning of the urinary tract) or suffering from sexual dysfunctions such as, for example, female sexual arousal disorders and female sexual orgasmic disorders.

One of skill in the art will appreciate that suitable formulations are dependent on the form of delivery to be employed, and all such forms are contemplated by the present invention. Additionally, in some embodiments, combinations of agents are employed in a single formulation, while in other embodiments, agents are formulated separately, but administered in combination, or sequentially. In the discussion below, compositions of single agents will be understood to also include compositions of two or more agents. Still further, different formulations can be used for those embodiments in which agents are administered separately or sequentially, by different routes of administration.

The compounds of the present invention can be formulated to be administered using any of a variety of routes, including, e.g., oral, intravenous, intramuscular, subcutaneous, oral, pulmonary, transdermal, nasal, cervical, vaginal, buccal, anorectal, urethral for systemic or local delivery or, preferably, topical administration, such as, e.g., to the urethral or genital tract, for prophylactic and/or therapeutic treatment. The compounds of the present invention can also be administered by installation into the bladder.

The present compounds can be incorporated into a variety of compositions for therapeutic and/or prophylactic administration. A number of suitable formulations for use in the present invention are found in Remington, *Pharmaceutical Sciences*, Mack Publishing Company, Philadelphia, Pa., 17th ed. (1985); and in *Dermatological Formulations: Percutaneous absorption*, Barry (Ed.), Marcel Dekker Inc. (1983). Moreover, for a brief review of methods for drug delivery, see, Langer, *Science,* 249:1527–1533 (1990). The pharmaceutical compositions described herein can be manufactured in a manner that is known to those of skill in the art, i.e., by means of conventional mixing, dissolving, levigating, emulsifying, encapsulating, entrapping or lyophilizing processes. It will be appreciated that the present methods and excipients are merely exemplary and are in no way limiting.

A. Topical Formulations

In view of the above, the present invention provides topical compositions useful for treating urogenital disorders and for treating spasms of mammals, including humans, which comprise an effective amount of a compound that reduces the contraction of the musculature of the vagina and a pharmaceutically acceptable carrier. The compound for use in the topical compositions of the present invention include, but are not limited to, NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators, endothelin receptor antagonists, bisphosphonates and cGMP-dependent protein kinase activators (e.g., cGMP mimetics).

In related embodiments, the present invention provides topical pharmaceutical compositions in unit dosage form comprising per unit dosage an amount of the compound or combination provided above, which is effective for treating a urogenital disorder in a subject in need of such treatment. Typically the compounds are in combination with a pharmaceutically acceptable carrier. Such compositions are useful for treating or reducing pain associated with urogenital disorders, such as vaginal pain, lower abdominal pain, urinary tract pain, vulvar pain, pain associated with sexual intercourse, and for treating spasms of the musculature of the vagina, in particular of the lower third of the vagina. The topical compositions of the invention are also useful for treating conditions associated with spasms of the musculature of the vagina, including vaginismus and dyspareunia. In addition, the topical compositions described herein are useful for relaxing the musculature of the lower third of the vagina and reducing pain before, during and after gynecological examinations, insertion of instruments and procedures, such as surgery.

Dosage forms for the topical administration of the compounds of this invention include powders, sprays, ointments, pastes, creams, lotions, gels, solutions, patches, suppositories and liposomal preparations. The dosage forms may be formulated with mucoadhesive polymers for sustained release of active ingredients at the urogenital area. The active compound may be mixed under sterile conditions with a pharmaceutically acceptable carrier, and with any preservatives, buffers, or propellants, which may be required. Topical preparations can be prepared by combining the compound of interest with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Lotions may be formulated with an aqueous or oily base and, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or nonaqueous base also comprising one or more dispersing agents, suspending agents, solubilizing agents, and the like.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Representative compositions include topical compositions comprising one or more of the following first pharmacological compounds: NO donors, calcium channel blockers, cholinergic modulators, α-adrenergic receptor antagonists, β-adrenergic receptor agonists, phosphodiesterase inhibitors, cAMP-dependent protein kinase activators (e.g., cAMP mimetics), superoxide scavengers, potassium channel activators, estrogen-like compounds, testosterone-like compounds, benzodiazepines, adrenergic nerve inhibitors, antidiarrheal agents, HMG-CoA reductase inhibitors, smooth muscle relaxants, adenosine receptor modulators, adenylyl cyclase activators, endothelin receptor antagonists, bisphosphonates and cGMP-dependent protein kinase activators (e.g., cGMP mimetics) in combination with a pharmaceutically acceptable carrier and at least one of the following second pharmacologic agents: a local anesthetic (e.g., lidocaine, prilocaine, etc.), local anti-inflammatory agent (e.g., naproxen, pramoxicam, etc.), corticosteroid (e.g., cortisone, hydrocortisone, etc.), anti-itch agent (e.g., loperamide, diphylenoxalate, etc.), an agent that interferes with the activation of peripheral sensory neurons, including divalent and trivalent metal ions (e.g., manganese, calcium, strontium, nickel, lanthanum, cerium, zinc, etc.), analgesic agents, yeast-based product (e.g., lyophilized yeast, yeast extract, etc.), growth-promoting and/or wound healing-promoting agent known to promote re-epithelialization (e.g., platelet-derived growth factor (PDGF), interleukin-11 (IL-11), etc.), anti-microbial agent (e.g., Neosporin, polymyxin B sulfate, bacitracin zinc, etc.), mucoadhesive agent (e.g., cellulose derivatives, etc.), cytoprotectant agent (e.g., colloidal bismuth, misoprostol, sucralfate, etc.) as defined in Goodman and Gilman, *The Pharmacological Basis of Therapeutics*, supra, or menthol. The at least one first pharmacological compound is typically present in the composition in unit dosage form effective for the treatment of a first medical condition(s), such as a urogenital disease or pain associated. The at least one second pharmacological compound is typically present in the composition in unit dosage effective for the treatment of a second medical condition(s), or a condition(s), symptom(s) or effect(s) associated with or resulting from the first medical condition(s).

The topical pharmaceutical compositions can also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

One example of a topical formulation includes 75% (w/w) white petrolatum USP, 4% (w/w) paraffin wax USP/NF, lanolin 14% (w/w), 2% sorbitan sesquioleate NF, 4% propylene glycol USP, and 1% compound of the present invention.

The dosage of a specific compound depends upon many factors that are well known to those skilled in the art, for example, the particular compound; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

B. Sustained or Controlled Delivery Formulations

In yet other embodiments, the invention provides topical sustained and prolonged release pharmaceutical compositions comprising one or more pharmacological compounds described supra, and a pharmaceutically acceptable carrier, to treat urogenital disorders. Such compositions are useful in the treatment of such urogenital disorders and in controlling and reducing pain associated therewith. Such compositions may comprise a unit dosage of one or more particular active agent(s) (e.g., a NO donor, calcium channel blocker, cholinergic modulator, α-adrenergic receptor antagonist, β-adrenergic receptor agonist, phosphodiesterase inhibitor, cAMP-dependent protein kinase activator, superoxide scavenger, potassium channel activator, estrogen-like compound, testosterone-like compound, benzodiazepine, adrenergic nerve inhibitor, antidiarrheal agent, HMG-CoA reductase inhibitor, smooth muscle relaxant, adenosine receptor modulator, adenylyl cyclase activator, cAMP mimetic, endothelin receptor antagonist, bisphosphonate, cGMP-dependent protein kinase activator, cGMP mimetic) which is effective in treating urogenital disorders and in controlling and alleviating pain associated therewith. Preferably, the compositions are administered in unit dosage form to a subject in need of such treatment. Topical sustained and prolonged release compositions are typically variants which include 1) an absorbent in a hydrophilic base; 2) an absorbent in a hydrophobic base; and 3) coated beads containing an absorbent matrix dispersed in a suitable vehicle. Also provided are methods of treating urogenital disorders comprising topically administering an effective amount of such compositions (e.g., in unit dosage form) to the appropriate urogenital area of the subject in need of such treatment.

Such hydrophilic compositions and preparations of the invention comprise a compound of the invention and a polymer, such as cellulose (methyl cellulose, ethyl cellulose, hydroxy propyl cellulose, etc.), higher molecular weight polyethylene glycol, methacrylic-acrylic acid emulsion, hydrogel, carbopol, ethyl vinyl acetate copolymer, or polyester, etc., to bind the compound of interest to the polymer. The compound-polymer matrix is then dispersed in a hydrophilic vehicle to form a semi-solid. After administration of such hydrophilic composition into the appropriate urogenital area, such as, e.g., the vagina or urethral tract, the water in the semi-solid preparation is adsorbed and the polymer matrix with the active ingredient (i.e., the pharmaceutical compound) remains as a coating in the area to which it has been applied. The pharmaceutical compound is then slowly released from this coating.

Hydrophobic compositions and preparations of the invention employ similar polymers as used in the hydrophilic preparations, but the polymer/compound matrix is dispersed into a vehicle, such a plastibase, in the hydrophobic compositions and preparations. Plastibase is a mineral oil base that only partially dissolves the pharmaceutical compound. The semi-solid composition forms a thin coating on the urogenital region to which the composition has been applied (such as, e.g., the vagina or urethral tract) and slowly releases the active compound. The prolonged action is controlled principally by the solubility of the active ingredient in the vehicle.

The present invention also provides coated beads which are produced by first absorbing a compound of the present invention, or a combination of compounds, on a cellulosic material blended with polyethylene glycol, filler, binder and other excipients. The resulting matrix is then extruded and spheronized (e.g., the process of making into spheres) to create small beads. The beads are then coated to an appropriate thickness with one or more of a suitable material, such as a methacrylic-acrylic polymer, polyurethane, ethyl vinyl acetate copolymer, polyester, silastic, etc. The coating on the beads acts as a rate controlling membrane that regulates the release of the compound from the core beads.

In other embodiments, the invention provides pharmaceutical compositions suitable for oral administration which are provided in unit dosage form comprising per unit dosage a NO donor, calcium channel blocker, cholinergic modulator, α-adrenergic receptor antagonist, β-adrenergic receptor agonist, phosphodiesterase inhibitor, cAMP-dependent protein kinase activator, superoxide scavenger, potassium channel activator, estrogen-like compound, testosterone-like compound, benzodiazepine, adrenergic nerve inhibitor, antidiarrheal agent, HMG-CoA reductase inhibitor, smooth muscle relaxant, adenosine receptor modulator, adenylyl cyclase activator, cAMP mimetic, endothelin receptor antagonist, bisphosphonate, cGMP-dependent protein kinase activator, cGMP mimetic, and a pharmaceutically acceptable carrier. Such compositions are useful for treating urogenital disorders, including those disorders and conditions described above.

For delivery to the buccal membranes, typically an oral formulation, such as a lozenge, tablet, or capsule is used. Methods of manufacture of these formulations are known in the art, including but not limited to, the addition of a pharmacological agent to a pre-manufactured tablet; cold compression of an inert filler, a binder, and either a pharmacological compound or a substance containing the compound (as described in U.S. Pat. No. 4,806,356); and encapsulation. Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa. The compounds of the present invention can be incorporated into these formulations as well.

C. Aerosol Formulations

For delivery to the nasal or bronchial membranes, typically an aerosol formulation is employed. The term "aerosol" includes any gas-borne suspended phase of the pharmacological agent that is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a pharmacological compound of interest suspended in air or other carrier gas, which may be delivered by insulation from an inhaler device, for example. For solutions used in making aerosols, the preferred range of concentration of the pharmacological agent is 0.1–100 mg/ml, more preferably 0.1–30 mg/ml, and most preferably, 1–10 mg/ml. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington, *Pharmaceutical Sciences*, see also, Ganderton, et al., *Drug Delivery to the Respiratory Tract*, Ellis Horwood (1987); Gonda, *Critical Reviews in Therapeutic Drug Carrier Systems*, 6:273–313 (1990); and Raeburn, et al., *J. Pharmacol. Toxicol. Methods*, 27:143–159 (1992).

IV. Methods of Treating Urogenital Disorders

In another aspect, the present invention provides methods for treating urogenital disorders which comprise administering to an appropriate area or affected urogenital tissue (e.g., vagina or urinary tract) of a subject in need of such treatment an effective amount of any of the compositions provided above. By use of such methods of the invention, spasms of the musculature of the vagina are relieved and signs and symptoms associated with urogenital disorders, e.g., vaginismus, dyspareunia, vulvodynia, vulvar vestibulitis, nonspecific urethritis (i.e., nonspecific pain, itching or burning of the urinary tract), interstitial cystitis, and pain associated therewith are improved. The methods described herein are also applicable to the treatment of recurrent urogenital diseases, and are also useful for relaxing the musculature of the vagina and reducing pain during gynecological exams (in patients with and without disorders), particularly during procedures where instruments are inserted into the vagina. The methods and compounds described herein are also useful for increasing a condition selected from the group consisting of vaginal lubrication, clitoral or labial sensitivity and engorgement and relaxation of vaginal smooth muscle.

The present invention further provides methods of using the above-described compositions in combination with local anesthetic agents, such as, for example, lidocaine, prilocaine, etc. Each of the compositions will typically be in a pharmaceutically acceptable dosage form as an effective treatment for a urogenital medical condition. These pharmaceutical preparations are also useful in treating conditions associated with or resulting from spasms of the musculature of the vagina including, but not limited to, vaginismus and dyspareunia. In another aspect, the present invention provides methods for treating urogenital disorders which comprise administering an effective amount of one a composition described herein along with a local anesthetic agent to a subject in need of such treatment. Such compositions can be administered orally, transdermally, transmucosally or parenterally.

Similarly, the invention provides methods of using the above-described compositions in combination with local anti-inflammatory agents, for example, naproxen or piroxicam, in a pharmaceutically acceptable dosage form as an effective treatment for a urogenital medical condition such as, e.g., vaginismus, dyspareunia, vulvodynia, vulvar vestibulitis, nonspecific urethritis (i.e., nonspecific pain, itching or burning of the urinary tract), interstitial cystitis, etc. These pharmaceutical preparations are also useful in treating conditions associated with spasms of the musculature of the vagina. In another aspect, the present invention provides methods for treating urogenital disorders which comprise administering an effective amount of such composition along with a local anesthetic agent to a subject in need of such treatment. Such compositions can be administered orally, transdermally, transmucosally or parenterally.

Additional methods provided by the present invention are those in which two or more agents selected from a NO donor, calcium channel blocker, cholinergic modulator, α-adrenergic receptor antagonist, β-adrenergic receptor agonist, phosphodiesterase inhibitor, cAMP-dependent protein kinase activator, superoxide scavenger, potassium channel activator, estrogen-like compound, testosterone-like compound, benzodiazepine, adrenergic nerve inhibitor, antidiarrheal agent, HMG-CoA reductase inhibitor, smooth muscle relaxant, adenosine receptor modulator, adenylyl cyclase activator, cAMP mimetic, endothelin receptor antagonist, bisphosphonate, cGMP-dependent protein kinase activator, cGMP mimetic, are administered either in combination or sequentially to provide an enhanced therapeutic benefit. The use of two compounds from those listed above can provide fewer and less severe side effects than equally effective doses of a single compound, if used alone. More particularly, the use of two compounds in combination allows for decreased amounts of each compound to be used to achieve the same benefit relative to a compound used alone, and provides significantly reduced occurrence and duration of side effects.

EXAMPLES

Example 1

Minoxidil ointment was prepared using the following formulation and procedure:

| Ingredient | Formulation: Supplier | % weight per weight |
|---|---|---|
| Minoxidil, USP | Spectrum Chemical | 0.20 |
| White Petrolatum, USP | Penreco, Inc. | 82.80 |
| Paraffin Wax, USP | Spectrum Chemical | 5.00 |
| Propylene Glycol, USP | Spectrum Chemical | 8.00 |
| Sorbitan Sesquioleate, NF | Spectrum Chemical | 4.0 |

Procedure:
1. Weigh all ingredients, record weights, and label appropriately.
2. Heat the propylene glycol to 40° C. with stirring and maintain.
3. Add the Minoxidil to the warm propylene glycol from step 1 and stir until dissolved.
4. Add the sorbitan sesquioleate to the solution in step 2 and homogenize until a suspension forms.
5. In a separate container, heat and melt the paraffin wax with gentle stirring, until a single clear phase is formed. Record temperature and maintain.
6. Heat the white petrolatum to between 70° C. and 75° C. in the bowl of mixer.
7. Add and mix the melted wax from step 5 to the melted petrolatum from step 6.
8. Paddle mix the blend from step 7 while air cooling to 50° C.
9. When the petrolatum-paraffin wax solution has reached 50° C., stop the paddle mixing and place a homogenizer in the bowl and pour in the warm suspension from step 3 while mixing at moderate speed. Homogenize at moderate speed for 10 minutes.
10. Replace the paddle on the mixer and paddle mix the suspension from step 9 on slow speed until the product had cooled below 30° C.
11. Package the product in screw capped glass jars and label appropriately.

Minoxidil ointment concentrations ranging from 0.05% w/w to 2.0% w/w can be made by modifying the amounts of the excipients listed in the above formulation, and using the same procedure as given above.

Example 2

Aminophylline cream was prepared using the following formulation and procedure:

| Ingredient | Formulation: Supplier | % weight per weight |
|---|---|---|
| Aminophylline, USP | Spectrum Chemical | 1.00 |
| Purified Water, USP | Baxter, Inc. | 87.25 |
| Cetostearyl Alcohol | Spectrum Chemical | 7.50 |
| Bridj 58 | Spectrum Chemical | 3.75 |
| Imidurea | Spectrum Chemical | 0.50 |

Procedure:
1. Weigh all ingredients, record weights, and label appropriately.
2. Add the Cetostearyl Alcohol and Bridj 58 to a suitable vessel. Heat with stirring until the melted waxes reach between 70° C. and 75° C. and maintain.
3. Heat the Purified Water in a separate vessel to between 60° C. and 65° C. with stirring.
4. Add the Imidurea to the hot water from step 3 and stir until dissolved.
5. Dissolve the Aminophylline in the mixture from step 4 with stirring and immediately proceed to step 6.
6. Place an homogenizer in the aqueous solution from step 5 and homogenize at slow to moderate speed while adding the hot melted waxes from step 2.
7. Allow the emulsion formed in step 6 to cool to between 40° C. and 45° C. and maintain while homogenizing at slow to moderate speed.
8. Remove the homogenizer from the emulsion formed in step 6 and insert a propeller mixer. Mix with the propeller mixer at slow speed while allowing the cream to cool to below 30° C.
9. Package the product in screw capped glass jars and label appropriately.

Aminophylline cream concentrations ranging from 0.05% w/w to 10.0% w/w can be made by modifying the amounts of the excipients listed in the above formulation, and using the same procedure as given above.

Example 3

Patients are first diagnosed with vaginismus, and the Vaginismus Behavior Scale (VABESC) score (Wijma, et al., *Scand. J. Behaviour Therapy*, 26(4):147–156 (1997)) for each patient is recorded at baseline. Nitroglycerin ointment is applied intravaginally to the outer one third of the vagina, once to four times daily to relax the vaginal muscle. Nitroglycerin ointment can also be applied to the vaginal opening as frequently as needed to achieve the desired effect. Alternatively, nitroglycerin ointment can be applied 5 to 15 minutes before intercourse to relax the vaginal muscle; thus allowing for successful intercourse, either with or without significant changes in VABESC score. The nitroglycerin ointment concentration varies between 2.0% (w/v) to 0.05%, more preferably, between 0.1% to 0.6% to achieve the desired effect. The desired effects include, but are not limited to, immediate pain relief, local tissue relaxation, and increase in blood flow. Patients may also use commercially available Nitro-Bid®, Percutol® or Rectogesic® ointments as is or by diluting to the appropriate concentration.

Example 4

Patients are first diagnosed with vaginismus, and the VABESC score for each patient is recorded at baseline. Under physician assistance, an intrauterine device (IUD) containing diltiazem, a calcium channel blocker, is inserted into the patient's uterus. The controlled and continuous release of diltiazem from the IUD allows for relaxation of the vaginal muscle and thus, vaginal penetration during coitus. If desired, patients using a diltiazem IUD can also apply nitroglycerin ointment before intercourse to maximize the relaxation.

Example 5

Patients are first diagnosed with vaginismus, and the VABESC score for each patient is recorded at baseline. If patients do not have other cardiovascular disease complication, oral nifedipine or other calcium channel blocker tablets (or caplets, capsules, etc.) can be administered, approximately 45 minutes to 4 hours before coitus to produce the desired effects. Alternatively, patients can take the calcium channel blocker orally once to three times daily and apply nitroglycerin ointment or topical diltiazem cream before intercourse to maximize the desired effects. The desired effects can include immediate pain relief, local tissue relaxation, and increased blood flow.

Example 6

Patients are first diagnosed with vaginismus and the VABESC score for each patient is recorded at baseline. Topical aminophylline cream is applied either externally to the vaginal opening or internally to the outer one third of the vaginal canal to achieve pain relief, muscle relaxation, and increased blood flow. Alternatively, vaginal suppositories or tablets containing aminophylline are inserted once daily or as needed to achieve the desired effects.

Example 7

Patients are first diagnosed with dyspareunia, e.g., superficial, vaginal or deep dyspareunia. Depending on the site of disease manifestation, topical loperamide solution is applied to the site either before intercourse to prevent pain, or after intercourse 1–4 times daily for several consecutive days for relief of pain. Pain prevention or relief is further improved by using either nitroglycerin ointment or a diltiazem cream in conjunction with or sequentially with the loperamide solution. The concentration of diltiazem cream is 4.0% (w/v) to 0.5%; more preferably, the diltiazem cream concentration is 3–1%, depending upon the efficacy.

Example 8

Patients diagnosed with vulvar vestibulitis are treated with nifedipine ointment topically to the site of the disease once or multiple times each day until the symptoms are reduced. Once vulvar vestibulitis is no longer debilitating, nonpainful intercourse can be attained by the individual. Alternatively, patients can take anti-inflammatory agents, such as glucocorticoids or NSAIDS, as recommended by the physician. Subsequently, topical calcium channel blocker cream, e.g., diltiazem cream, is applied before intercourse to facilitate nonpainful coitus.

Example 9

Patients suffering from Interstitial Cystitis (IC) have either ulcerative or nonulcerative IC. In order to mitigate the symptoms associated with IC, a vaginal ring containing lovastatin is inserted into the vagina. The continuous release of lovastatin greatly facilitates the relief of these debilitating symptoms. Alternatively, patients can take anti-inflammatory agents, such as glucocorticoids or NSAIDS, orally at the frequency recommended by the physician while the lovastatin vaginal ring is in place. Another approach is to take oral antibiotic while patients are using the lovastatin vaginal ring to further expedite the relief of symptoms.

Example 10

Four patients with vestibulitis and secondary vaginismus were recruited to the study. All patients were given 0.2% nitroglycerin (NTG) ointment for use on an as needed basis. Patients were instructed to apply an effective amount of the nitroglycerin ointment to the affected area. Some of these patients have used either Estrogen cream, MetroGel or anti-yeast products previously, did not respond to these therapies, and were having major difficulty in conducting normal sexual activity. Following the 0.2% NTG treatment, all patients experienced significant improvement in pain reduction and have been able to conduct normal sexual activity after the therapy. Some of the symptomatic relief, such as pain reduction, was immediate. None of the four patients reported adverse reaction; no headaches or dizziness was reported in the study. It was concluded that the treatment with nitroglycerin ointment was effective in treating patients with both vestibulitis and vaginismus.

Example 11

Example 9 demonstrates the relief of vaginal and labial pain and burning with 0.2% nitroglycerin ointment in women with vulvodynia. Patients with a documented history of vulvodynia received 0.2% NTG ointment (⅛teaspoon) (Nitro-Bid® ointment, Aventis Pharmaceuticals, Parsippany, N.J., diluted to 0.2% with white petrolatum) in the office and were then instructed to use it on an as needed basis prior to sexual relations at home. Each patient completed a questionnaire assessing frequency of use, dosage, location applied, satisfaction, and side effects. A standardized pain scale was used to rate pain pre and post treatment.

A total of 12 women with a primary complaint of pain in the vaginal and labial area received medication. Mean age was 32 years. Pain had been present from 5 months to 6 years prior to the initiation of treatment. 8 of the 12 patients completed the study. All 12 patients had reproducible pain in the office that was relieved within 5 minutes of application. 2 did not use the ointment outside of the office setting due to headache. The remaining 6 had significantly decreased pain intensity on a scale of 0 (no pain) to 5 (excruciating pain); (4.3 to 1.4 p<0.01) at 3 months follow up. All of the patients reported "improvement" of pain during sexual activity. No adverse advents occurred.

Treatment with 0.2% NTG ointment was effective in providing temporary relief of vaginal pain and labial pain in women with vulvodynia. In particular, application of 0.2% NTG applied prior to sexual activity significantly decreased pain related to vaginal penetration. Although well tolerated, headache occurred in the majority of women. Thus, lower doses of nitroglycerin would be advantageous in controlling or limiting the occurrence of this side effect. Preferred concentrations are below 0.2%, and range from about 0.01% to about 0.1%.

Example 12

Patients are first diagnosed with vaginismus, and the Vaginismus Behaviour Scale (VABESC) score may be recorded at baseline. Yohimbine ointment is applied intravaginally to the outer one third of the vagina, once to four times daily to relax the vaginal muscle. Yohimbine ointment can also be applied to the vaginal opening as frequently as needed to achieve the desired effect. Alternatively, yohimbine ointment can be applied before intercourse to relax the vaginal muscle; thus allowing for successful intercourse, either with or without significant changes in VABESC score. Preferably, the ointment is applied 5 minutes to one hour before intercourse to achieve the desired effect on the vaginal muscle. The yohimbine ointment concentration varies between 2.0% (w/v) to 0.05%, preferably, between 0.05% to 0.1%. or 0.1% to 0.5%, to achieve the desired effect. The desired effects include, but are not limited to, immediate pain relief, local tissue relaxation, and increase in blood flow.

Example 13

Patients are first diagnosed with vaginismus, and the Vaginismus Behaviour Scale (VABESC) score may be recorded at baseline. Yohimbine tablets (10 mg) are taken orally, once to four times daily to relax the vaginal muscle. Additionally, yohimbine ointment can also be applied to the vaginal opening as frequently as needed to achieve the desired effect. Alternatively, in addition to administration of yohimbine tablets, yohimbine ointment can be applied before intercourse to relax the vaginal muscle; thus allowing for successful intercourse, either with or without significant changes in VABESC score. Preferably, the ointment is applied 5 minutes to one hour before intercourse to achieve the desired effect on the vaginal muscle. The yohimbine ointment concentration varies between 2.0% (w/v) to 0.05%, preferably, between 0.05% to 0.1%. or 0.1% to 0.5%, to achieve the desired effect. The desired effects include, but are not limited to, immediate pain relief, local tissue relaxation, and increase in blood flow.

Example 14

Benzodiazepines can be useful in achieving vaginal smooth muscle relaxation. For instance, patients may be first diagnosed with vaginismus, and the Vaginismus Behavior Scale (VABESC) score (Wijma, B. et al., Scand. J. Behavior Therapy, 1997, 26(4), 147–156) for each patient recorded at baseline. Diazepam (a benzodiazepine) ointment is applied intravaginally to the outer one third of the vagina, once to four times daily to relax the vaginal muscle. The diazepam ointment can also be applied to the vaginal opening as frequently as needed to achieve the desired effect. Alternatively, the diazepam ointment can be applied before intercourse to relax the vaginal muscle; thus allowing for successful intercourse, either with or without significant changes in VABESC score. Preferably, the ointment is applied 5 minutes to one hour before intercourse to achieve the desired effect on the vaginal muscle. The diazepam ointment concentration varies between 2.0% (w/v) to 0.05%, preferably, between 0.05% to 0.1%. or 0.1% to 0.5%, to achieve the desired effect. The desired effects include, but are not limited to, immediate pain relief, local tissue relaxation, and increase in blood flow.

Example 15

Patients are first diagnosed with dyspareunia, e.g., superficial, vaginal or deep dyspareunia. Depending on the site of disease manifestation, a topical vesamicol solution or ointment is applied to the site either before intercourse to prevent pain, or after intercourse 1–4 times daily for several consecutive days for relief of pain. Pain prevention or relief may be further improved by using either nitroglycerin ointment or a diltiazem cream in conjunction with or sequentially with the vesamicol. The concentration of diltiazem cream is 4.0% (w/v) to 0.5%; more preferably, the diltiazem cream concentration is 3–1%, depending upon the efficacy.

Example 16

An $\alpha_2$-adrenergic receptor antagonist may be useful in the treatment of patients in need of vaginal smooth muscle relaxation. For instance, patients may be first diagnosed with dyspareunia, e.g., superficial, vaginal or deep dyspareunia. Depending on the site of disease manifestation, a topical $\alpha_2$-adrenergic receptor antagonist (e.g., yohimbine) solution is applied to the site either before intercourse to prevent pain, or after intercourse 1–4 times daily for several consecutive days for relief of pain. Pain prevention or relief may be further improved by using either nitroglycerin ointment or a diltiazem cream in conjunction with or sequentially with the yohimbine. The concentration of diltiazem cream is 4.0% (w/v) to 0.5%; more preferably, the diltiazem cream concentration is 3–1%, depending upon the efficacy.

In the case of yohimbine, this compound can be formulated in an aqueous formulation of up to 0.8% in sterile water. Yohimbine may also be formulated as topical composition comprising an aqueous or slightly alcoholic gel or in a cream or lotion for direct application to the urogenital region.

Example 17

Acetylcholine storage blockers may be useful in patients in need of vaginal smooth muscle relaxation. For instance, patients may be first diagnosed with vaginismus, and the Vaginismus Behaviour Scale (VABESC) score recorded. An acetylcholine storage blocker (e.g., vesamicol) ointment is applied intravaginally to the outer one third of the vagina, once to four times daily to relax the vaginal muscle. The ointment can also be applied to the vaginal opening as frequently as needed to achieve the desired effect. Alternatively, the ointment can be applied before intercourse to relax the vaginal muscle; thus allowing for successful intercourse, either with or without significant changes in VABESC score. Preferably, the ointment is applied 5 minutes to one hour before intercourse to achieve the desired effect on the vaginal muscle. When the acetylcholine storage blocker is vesamicol, the vesamicol ointment concentration varies between 2.0% (w/v) to 0.05%, preferably, between 0.05% to 0.1%. or 0.1% to 0.5%, to achieve the desired effect. The desired effects include, but are not limited to, immediate pain relief, local tissue relaxation, and increase in blood flow.

Vesamicol can be applied in an aqueous gel or lotion type of formulation.

Example 18

Adenosine receptor modulators, may be useful in patients in need of vaginal smooth muscle relaxation. For instance, patients may be first diagnosed with vaginismus, and the Vaginismus Behaviour Scale (VABESC) score recorded. An adenosine receptor modulator (e.g., theophylline or dyphylline) ointment is applied intravaginally to the outer one third of the vagina, once to four times daily to relax the vaginal muscle. The ointment can also be applied to the vaginal opening as frequently as needed to achieve the desired effect. Alternatively, the ointment can be applied before intercourse to relax the vaginal muscle; thus allowing for successful intercourse, either with or without significant changes in VABESC score. Preferably, the ointment is applied 5 minutes to one hour before intercourse to achieve the desired effect on the vaginal muscle. The adenosine receptor modulator ointment concentration varies between 2.0% (w/v) to 0.05%, preferably, between 0.05% to 0.1%. or 0.1% to 0.5%, to achieve the desired effect. The desired effects include, but are not limited to, immediate pain relief, local tissue relaxation, and increase in blood flow.

Example 19

An adenosine receptor modulator may be useful in the treatment of patients in need of vaginal smooth muscle relaxation. For instance, patients may be first diagnosed with dyspareunia, e.g., superficial, vaginal or deep dyspareunia. Depending on the site of disease manifestation, a topical adenosine receptor modulator (e.g., theophylline or dyphylline) ointment is applied to the site either before intercourse to prevent pain, or after intercourse 1–4 times daily for several consecutive days for relief of pain. Pain prevention or relief may be further improved by using either nitroglycerin ointment or a diltiazem cream in conjunction with or sequentially with the yohimbine. The concentration of diltiazem cream is 4.0% (w/v) to 0.5%; more preferably, the diltiazem cream concentration is 3–1%, depending upon the efficacy.

Example 20

Menopausal women (either due to surgical or natural causes) complaining of loss of libido and/or pain during intercourse are first tested for the gonadal hormone levels. Specifically, the levels of testosterone (total, free and bioavailable), estradiol, DHEA, and DHEA-sulfate for the women are determined and compared to the normal levels observed in young healthy women (those not taking any hormonal medication such as oral contraceptives). If there a deficiency is found in the Androgen levels, the women will be prescribed Androgen replacement therapy (for example, topical testosterone gel or an oral DHEA supplement). Alternatively, if only the estrogen level is low, the women can be placed on the standard ERT (estrogen replacement therapy, e.g., Premarin®) with or without progestin, depending on whether the women still have intact uteruses. In the case when both estrogen and androgen levels are lower than those observed in young health women, EstraTest or EstraTest HS, (topical testosterone gel in combination with a topical estrogen gel) can be used to the treat the hormonal deficiency. If dyspareunia continues following a three to six month course of hormone replacement therapy, additional medication can be used to treat the problem. Under this scenario, women should continue their respective hormonal therapy and use topical vesamicol ointment before engaging in sexual intercourse.

Example 21

Patients complaining of recurrent pain, itching or burning of the urinary tract will be evaluated for signs of inflammation and infection, previous history of pelvic floor surgery, and any other signs of pathology. If they are found to be free of any of these medical conditions and yet still have ongoing pain, itching or burning of the urinary tract, topical treatment with nitroglycerin will be prescribed. A 0.2% topical nitroglycerin ointment will be applied to the affected area, either once daily or as frequent as needed to achieve efficacy, depending on the severity of the symptoms. The efficacy of relief can be evaluated based on a visual analog scale of 10 cm or on the patients' self-assessment. If the patients are diagnosed with minor infection, topical nitroglycerin ointment can be used in conjunction with antibiotic treatment to facilitate faster relief of symptoms.

Example 22

Patients complaining of inflammation of the urethra will be evaluated for signs of inflammation and infection, and any other signs of pathology. If they are found to be free of infection yet still have ongoing inflammation of the urethra, topical treatment with nitroglycerin will be prescribed. A 0.2% topical nitroglycerin ointment will be applied to the opening of the urethra and the surrounding area, either once daily or as frequent as needed to achieve efficacy, depending on the severity of the inflammation. The efficacy of relief can be evaluated based on a visual analog scale of 10 cm or on the patients' self-assessment.

Example 23

Women complaining of difficulty becoming aroused are first tested for the gonadal hormone levels. Specifically, the levels of testosterone (total, free and bioavailable), estradiol, DHEA, and DHEA-sulfate for the women are determined and compared to the normal levels observed in young healthy women (those not taking any hormonal medication such as oral contraceptives). If there a deficiency is found in the Androgen levels, the women will be prescribed Androgen replacement therapy (for example, topical testosterone gel or an oral DHEA supplement). Alternatively, if only the estrogen level is low, the women can be placed on the standard ERT (estrogen replacement therapy, e.g., Premarin®) with or without progestin, depending on whether the women still have intact uteruses. In the case when both estrogen and androgen levels are lower than those observed in young health women, EstraTest or EstraTest HS, (topical testosterone gel in combination with a topical estrogen gel) can be used to the treat the hormonal deficiency. If difficulty becoming aroused continues following a three to six month course of hormone replacement therapy, additional medication can be used to treat the problem. Under this scenario, women should continue their respective hormonal therapy and use topical minoxidil ointment before engaging in sexual intercourse. The minoxidil ointment concentration varies between 0.05% (w/v) to 5.0%, preferably, between 0.1% to 2.0%, to assist the patient in becoming aroused. The minoxidil ointment is applied intravaginally to the outer one third of the vagina, and to the clitoris and labia, once to four times daily. The minoxidil ointment can also be applied to the vaginal opening as frequently as needed to achieve the desired effect. Alternatively, the minoxidil ointment can be applied immediately before intercourse. Preferably, the cream is applied 5 minutes to one hour before intercourse to achieve the desired effect.

Example 24

Women complaining of difficulty reaching orgasm are first asked if they being treated with selective serotonin reuptake inhibitors (SSRI's). If they are taking SSRI's, they will be placed on a different SSRI to determine if the different SSRI will produce fewer sexual side-effects. If difficulty reaching orgasm continues following a three to six month course of therapy with the different SSRI, or if they are not receiving SSRI therapy, treatment with topical aminophylline cream can be used to treat the problem. The women will use topical aminophylline cream before engaging in sexual intercourse. The aminophylline cream is applied intravaginally to the outer one third of the vagina, once to four times daily. The aminophylline cream can also be applied to the vaginal opening as frequently as needed to achieve the desired effect. Alternatively, the aminophylline cream can be applied before intercourse; thus allowing for successful orgasm. Preferably, the cream is applied 5 minutes to one hour before intercourse to achieve the desired effect. The aminophylline cream concentration varies between 0.05% (w/v) to 5.0%, preferably, between 0.1% to 2.0%, to assist the patient in reaching orgasm.

Example 25

Women complaining of inadequate vaginal lubrication will be treated with topical aminophylline cream. The women will use topical aminophylline cream before engaging in sexual intercourse. The aminophylline cream is applied intravaginally to the outer one third of the vagina before engaging in sexual activity. The aminophylline cream can also be applied to the vaginal opening to achieve the desired effect. Alternatively, the aminophylline cream can be applied to the labia and clitoris. Preferably, the cream is applied 5 minutes to one hour before intercourse to achieve the desired effect. The aminophylline cream concentration varies between 0.05% (w/v) to 5.0%, preferably, between 0.1% to 2.0%, to increase vaginal lubrication.

Example 26

Women complaining of inadequate clitoral and/or labial sensitivity will be treated with topical minoxidil ointment. The women will use topical minoxidil ointment before engaging in sexual intercourse. The minoxidil ointment is applied intravaginally to the labia and clitoris before engaging in sexual activity. The minoxidil ointment can also be applied to the vaginal opening to achieve the desired effect. Alternatively, the minoxidil ointment can be applied to the outer one third of the vagina. Preferably, the ointment is applied 5 minutes to one hour before intercourse to achieve the desired effect. The minoxidil ointment concentration varies between 0.05% (w/v) to 5.0%, preferably, between 0.1% to 2.0%, to increase clitoral and/or labial sensitivity.

Example 27

Women complaining of inadequate clitoral and/or labial engorgement will be treated with topical minoxidil ointment. The women will use topical minoxidil ointment before engaging in sexual intercourse. The minoxidil ointment is applied intravaginally to the labia and clitoris before engaging in sexual activity. The minoxidil ointment can also be applied to the vaginal opening to achieve the desired effect. Alternatively, the minoxidil ointment can be applied to the outer one third of the vagina. Preferably, the ointment is applied 5 minutes to one hour before intercourse to achieve the desired effect. The minoxidil ointment concentration varies between 0.05% (w/v) to 5.0%, preferably, between 0.1% to 2.0%, to increase clitoral and/or labial engorgement.

All publications, patents and patent applications cited in this specification are herein incorporated by reference as if each individual publication, patent or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method for relieving the vulvar pain of vulvodynia in a patient, the method comprising topically administering to the affected vulvar area of the patient a NO donor in a therapeutically effective amount, wherein the vulvar pain which is not caused by dyspaerunia is relieved.

2. The method of claim 1, wherein the NO donor is nitroglycerin.

3. The method of claim 1, wherein said NO donor is in a form selected from the group consisting of gel, ointment, cream, lotion, powder, solution, suspension, spray, paste, oil, suppository, and foam.

4. The method of claim 1, wherein said NO donor is delivered continuously.

5. The method of claim 1, wherein the NO donor is formulated in a unit dosage.

6. The method of claim 1, wherein the patient is treated to prevent a relapse of vulvodynia.

7. The method of claim 1, wherein the patient is human.

8. The method of claim 1, wherein the vulvar pain of vulvodynia is constant.

9. The method of claim 1, wherein the vulvar pain of vulvodynia is intermittent.

10. The method of claim 1, wherein the vulvar pain of vulvodynia is diffuse.

11. The method of claim 1, wherein the vulvar pain of vulvodynia is localized.

12. The method of claim 1, wherein the NO donor is delivered locally by topical application in a sustained release format.

13. The method of claim 1, wherein the method consists essentially of administering the NO donor.

14. The method of claim 12, wherein the NO donor is nitroglycerin.

* * * * *